United States Patent [19]
Tang

[11] Patent Number: 6,132,424
[45] Date of Patent: Oct. 17, 2000

[54] SMOOTH AND UNIFORM LASER ABLATION APPARATUS AND METHOD

[75] Inventor: Fuqian Tang, Orlando, Fla.

[73] Assignee: LaserSight Technologies Inc., Winter Park, Fla.

[21] Appl. No.: 09/041,998

[22] Filed: Mar. 13, 1998

[51] Int. Cl.[7] .................................................. A61B 17/36
[52] U.S. Cl. .................................. 606/13; 606/5; 606/10; 606/17
[58] Field of Search .............................. 606/2, 4–6, 9–11, 606/13, 17, 18

[56] References Cited

U.S. PATENT DOCUMENTS

| | | |
|---|---|---|
| 2,480,737 | 8/1949 | Jayle . |
| 3,074,407 | 1/1963 | Moon . |
| 3,476,112 | 11/1969 | Elstein . |
| 3,697,889 | 10/1972 | Dewey, Jr. . |
| 3,743,965 | 7/1973 | Offner . |

(List continued on next page.)

FOREIGN PATENT DOCUMENTS

| | | |
|---|---|---|
| 1243732 | 10/1984 | Canada . |
| 0 151869 A1 | 8/1985 | European Pat. Off. . |
| 0296982A1 | 6/1988 | European Pat. Off. . |
| 0151869B1 | 1/1990 | European Pat. Off. . |
| 0368512A2 | 5/1990 | European Pat. Off. . |
| 0207648B1 | 8/1990 | European Pat. Off. . |
| 0418890A3 | 3/1991 | European Pat. Off. . |
| 0602756A1 | 6/1994 | European Pat. Off. . |
| PCT/FR87/ 00139 | 11/1987 | WIPO . |
| PCT/US92/ 09625 | 5/1993 | WIPO . |
| PCT/US93/ 00327 | 8/1993 | WIPO . |
| PCT/US94/ 02007 | 9/1994 | WIPO . |
| PCT/EP95/ 01287 | 10/1995 | WIPO . |

OTHER PUBLICATIONS

D. Eimeri, L. Davis, & S. Vlesko, Optical, mechanical, and thermal properties of barium borate, Journal of Applied Physics, Sep. 1987, pp. 1968–1983.

J.T. Lin, Non–linear crystals for tunable coherent sources, Optical and Quatum Electronics, 1990, pp. S283–S313.

J.T. Lin, Temperature–tuned noncritically phase–matched frequency conversion in LiB3O5 crystal, Optics Communications, Dec. 1990, pp. 159–165.

Y. Tanaka, H. Kuroda, & S. Shionoya, Generation of Tunable Picsecond Pulses in the Ultraviolet Region Down to 197nm, May 1982, pp. 434–436.

(List continued on next page.)

*Primary Examiner*—Linda C. M. Dvorak
*Assistant Examiner*—Bryan K. Yarnell
*Attorney, Agent, or Firm*—William H. Bollman; Farkas & Manelli PLLC

[57] ABSTRACT

A laser beam delivery apparatus and a method for smoothly and uniformly ablating tissue, e.g., for reshaping a cornea of an eye, even in the face of real-world conditions such as a moving eye. The method includes defining a plurality of scan lines in an ablation zone on the tissue and defining a plurality of laser beam ablation points along each of the scan lines. An ablating laser beam is scanned along a series of non-adjacent scan lines of the plurality of scan lines and tissue is intermittently ablated at non-adjacent ones of the laser beam ablation points on each non-adjacent scan line of the series of non-adjacent scan lines.

21 Claims, 3 Drawing Sheets

U.S. PATENT DOCUMENTS

| | | |
|---|---|---|
| 3,848,104 | 11/1974 | Locke . |
| 3,938,058 | 2/1976 | Yamamoto . |
| 3,982,541 | 9/1976 | L'Esperance, Jr. . |
| 3,983,507 | 9/1976 | Tang et al. . |
| 4,169,663 | 10/1979 | Murr . |
| 4,180,751 | 12/1979 | Ammann . |
| 4,349,907 | 9/1982 | Campillo et al. . |
| 4,386,428 | 5/1983 | Baer . |
| 4,423,728 | 1/1984 | Lieberman . |
| 4,461,294 | 7/1984 | Baron . |
| 4,477,159 | 10/1984 | Mizuno et al. . |
| 4,520,816 | 6/1985 | Schachar et al. . |
| 4,526,171 | 7/1985 | Schachar . |
| 4,538,608 | 9/1985 | L'Esperance, Jr. . |
| 4,546,773 | 10/1985 | Kremer et al. . |
| 4,573,467 | 3/1986 | Rich et al. . |
| 4,580,559 | 4/1986 | L'Esperance, Jr. . |
| 4,598,714 | 7/1986 | Kremer et al. . |
| 4,619,259 | 10/1986 | Graybill et al. . |
| 4,633,866 | 1/1987 | Peyman et al. . |
| 4,653,495 | 3/1987 | Nanaumi . |
| 4,662,370 | 5/1987 | Hoffman et al. . |
| 4,665,913 | 5/1987 | L'Esperance, Jr. . |
| 4,669,466 | 6/1987 | L'Esperance, Jr. . |
| 4,688,570 | 8/1987 | Kramer et al. . |
| 4,718,418 | 1/1988 | L'Esperance, Jr. . |
| 4,720,189 | 1/1988 | Heyman et al. . |
| 4,721,379 | 1/1988 | L'Esperance, Jr. . |
| 4,729,372 | 3/1988 | L'Esperance, Jr. . |
| 4,729,373 | 3/1988 | Peyman . |
| 4,732,148 | 3/1988 | L'Esperance, Jr. . |
| 4,764,930 | 8/1988 | Bille et al. . |
| 4,770,172 | 9/1988 | L'Esperance . |
| 4,773,414 | 9/1988 | L'Esperance, Jr. . |
| 4,784,135 | 11/1988 | Blum et al. . |
| 4,798,204 | 1/1989 | L'Esperance, Jr. . |
| 4,807,623 | 2/1989 | Lieberman . |
| 4,838,266 | 6/1989 | Koziol et al. . |
| 4,838,679 | 6/1989 | Bille . |
| 4,840,175 | 6/1989 | Peyman . |
| 4,848,340 | 7/1989 | Bille et al. . |
| 4,856,513 | 8/1989 | Muller . |
| 4,862,886 | 9/1989 | Clarke et al. . |
| 4,896,015 | 1/1990 | Taboada et al. . |
| 4,903,695 | 2/1990 | Warner et al. . |
| 4,907,586 | 3/1990 | Bille et al. . |
| 4,911,711 | 3/1990 | Telfair et al. . |
| 4,925,523 | 5/1990 | Braren et al. . |
| 4,941,093 | 7/1990 | Marshall et al. . |
| 4,968,130 | 11/1990 | Hideshima et al. . |
| 4,975,918 | 12/1990 | Morton . |
| 4,993,826 | 2/1991 | Yoder . |
| 4,994,058 | 2/1991 | Raven et al. . |
| 5,019,074 | 5/1991 | Muller . |
| 5,052,004 | 9/1991 | Gratze et al. . |
| 5,063,942 | 11/1991 | Kilmer et al. . |
| 5,065,046 | 11/1991 | Guyer . |
| 5,074,859 | 12/1991 | Koziol . |
| 5,102,409 | 4/1992 | Balgorod . |
| 5,108,388 | 4/1992 | Trokel . |
| 5,108,412 | 4/1992 | Krumeich et al. . |
| 5,133,726 | 7/1992 | Ruiz et al. . |
| 5,144,630 | 9/1992 | Lin . |
| 5,163,934 | 11/1992 | Munnerlyn . |
| 5,163,936 | 11/1992 | Black et al. . |
| 5,182,759 | 1/1993 | Anthon et al. . |
| 5,188,631 | 2/1993 | L'Esperance, Jr. . |
| 5,196,006 | 3/1993 | Klopotek et al. . |
| 5,207,668 | 5/1993 | L'Esperance, Jr. . |
| 5,217,452 | 6/1993 | O'Donnell . |
| 5,219,343 | 6/1993 | L'Esperance, Jr. . |
| 5,219,344 | 6/1993 | Yoder, Jr. . |
| 5,222,960 | 6/1993 | Poley . |
| 5,226,903 | 7/1993 | Mizuno . |
| 5,250,062 | 10/1993 | Hanna . |
| 5,257,988 | 11/1993 | L'Esperance, Jr. . |
| 5,263,950 | 11/1993 | L'Esperance, Jr. . |
| 5,284,477 | 2/1994 | Hanna et al. . |
| 5,288,292 | 2/1994 | Giraud et al. . |
| 5,290,301 | 3/1994 | Lieberman . |
| 5,312,320 | 5/1994 | L'Esperance, Jr. . |
| 5,324,281 | 6/1994 | Muller . |
| 5,334,190 | 8/1994 | Seiler . |
| 5,336,217 | 8/1994 | Buys et al. .................................. 606/9 |
| 5,345,534 | 9/1994 | Najm et al. . |
| 5,349,590 | 9/1994 | Amirkhanian et al. . |
| 5,350,374 | 9/1994 | Smith . |
| 5,353,262 | 10/1994 | Yakymyshyn et al. . |
| 5,360,424 | 11/1994 | Klopotek . |
| 5,363,388 | 11/1994 | Shi et al. . |
| 5,364,388 | 11/1994 | Koziol . |
| 5,370,641 | 12/1994 | O'Donnell, Jr. . |
| 5,395,356 | 3/1995 | King et al. . |
| 5,395,362 | 3/1995 | Sacharoff et al. . |
| 5,405,355 | 4/1995 | Peyman et al. . |
| 5,411,501 | 5/1995 | Klopotek . |
| 5,423,801 | 6/1995 | Marshall et al. . |
| 5,425,727 | 6/1995 | Koziol . |
| 5,425,729 | 6/1995 | Ishida et al. . |
| 5,437,658 | 8/1995 | Muller et al. . |
| 5,441,511 | 8/1995 | Hanna . |
| 5,442,487 | 8/1995 | Mizuno . |
| 5,445,633 | 8/1995 | Nakamura et al. . |
| 5,461,212 | 10/1995 | Seiler et al. . |
| 5,470,329 | 11/1995 | Sumiya . |
| 5,474,548 | 12/1995 | Knopp et al. . |
| 5,480,396 | 1/1996 | Simon et al. . |
| 5,505,723 | 4/1996 | Muller . |
| 5,507,741 | 4/1996 | L'Esperance, Jr. . |
| 5,507,799 | 4/1996 | Sumiya . |
| 5,520,679 | 5/1996 | Lin . |
| 5,549,597 | 8/1996 | Shimmick et al. . |
| 5,556,395 | 9/1996 | Shimmick et al. . |
| 5,582,752 | 12/1996 | Zair . |
| 5,599,340 | 2/1997 | Simon et al. . |
| 5,613,965 | 3/1997 | Muller . |
| 5,624,436 | 4/1997 | Nakamura et al. . |
| 5,634,920 | 6/1997 | Hohla . |
| 5,637,109 | 6/1997 | Sumiya . |
| 5,646,791 | 7/1997 | Glockler . |
| 5,651,784 | 7/1997 | Klopotek . |
| 5,683,379 | 11/1997 | Hohla . |
| 5,684,562 | 11/1997 | Fujieda . |
| 5,711,762 | 1/1998 | Trokel . |
| 5,713,892 | 2/1998 | Shimmick . |
| 5,735,843 | 4/1998 | Trokel . |
| 5,782,822 | 7/1998 | Telfair et al. . |
| 5,849,006 | 12/1998 | Frey et al. . |
| 5,865,830 | 2/1999 | Parel et al. . |
| 5,980,513 | 11/1999 | Frey et al. ................................ 606/10 |
| 3,848,104 | 11/1974 | Locke . |
| 3,938,058 | 2/1976 | Yamamoto . |
| 3,982,541 | 9/1976 | L'Esperance, Jr. . |
| 3,983,507 | 9/1976 | Tang et al. . |
| 4,169,663 | 10/1979 | Murr . |
| 4,180,751 | 12/1979 | Ammann . |
| 4,349,907 | 9/1982 | Campillo et al. . |
| 4,386,428 | 5/1983 | Baer . |
| 4,423,728 | 1/1984 | Lieberman . |
| 4,461,294 | 7/1984 | Baron . |
| 4,477,159 | 10/1984 | Mizuno et al. . |
| 4,520,816 | 6/1985 | Schachar et al. . |

| | | |
|---|---|---|
| 4,526,171 | 7/1985 | Schachar . |
| 4,538,608 | 9/1985 | L'Esperance, Jr. . |
| 4,546,773 | 10/1985 | Kremer et al. . |
| 4,573,467 | 3/1986 | Rich et al. . |
| 4,580,559 | 4/1986 | L'Esperance, Jr. . |
| 4,598,714 | 7/1986 | Kremer et al. . |
| 4,619,259 | 10/1986 | Graybill et al. . |
| 4,633,866 | 1/1987 | Peyman et al. . |
| 4,653,495 | 3/1987 | Nanaumi . |
| 4,662,370 | 5/1987 | Hoffman et al. . |
| 4,665,913 | 5/1987 | L'Esperance, Jr. . |

OTHER PUBLICATIONS

Qiushi Ren, Raymond P. Galitis, Keith P. Thompson, & J.T. Lin, "Ablation of the Cornea and Synthetic Polymers Using a UV (213nm) Solid State Laser", IEEE Journal of Quantum Electronics, Dec. 1990, pp. 2284–2288.

Conference on Lasers and Electro–Optics, Optical Society of America, May 1990, pp. 28–30.

G.P.A. Malcom, M.A. Persaud, & A.I. Ferguson, "Resonant Frequency Quadrupling of a Mode—Locked Diode—Pumped Nd: YLF Laser", Optics Letters, Jul. 1991, pp. 983–985.

J.T. Lin, J.L. Montgomery, "Temperature—Tuned Noncritically Phase—Matched Frequency Conversion in $LiB_3O_5$ Crystal", Optics Communications, Dec. 1990, pp. 159–165.

A.A. Babin, F.I. Fel'dshtein, & I.V. Yakovlev, "Generation of the Fifth Harmonic of Yttrium Orthoaluminate: $Nd^{3+}$ Laser Radiation in KDP at Room Temperatures", Soviet Technical Physics Letters, Jun. 1990, pp. 417–418.

V.D. Volosov & E.V. Nilov, "Effect of the Spatial Structure of a Laser Beam on the Generation of the Second Harmonic in ADP and KDP Crystals", UDC, Nov. 1965, pp. 715–719.

A.G. Arutyunyan, G.G. Gurzadyan, & R.K. Ispiryan, "Generation of the Fifth Harmonic of Picosecond Yttrium Aluminate Laser Radiation", Soviet Journal Quantum Electron, Dec. 1989, pp. 1602–1603.

Shinichi Imai, Toshitaka Yamada, Yasutomo Fujimori & Ken Ishikawa, Third—Harmonic Generation of an Alexandrite Laser in $\beta$–$BaB_2O_4$, Applied Physics Letters, May 1989, pp. 1206–1208.

Conference on Lasers and Electro–Optics, Optical Society of America, Apr. 1989, p. 390.

Barraquer, "Lamellar Keratoplasty (special techniques)" Annals of Ophthalmology, Jun. 1972, pp. 437–469.

Burnett, "Compnay Denies Delay in Approval for Laser", Orlando Sentinel, Feb. 1993, pp. 12–13.

Burnett, "Medical Technology", Orlando Sentinel, Feb. 1993, pp. 1–5.

Gailitis et al., "Solid State Ultraviolet Laser (213 nm) Ablation of the Cornea and Synthetic Collagen Lenticles", Lasers in Surgery and Medicine, Dec. 1991, pp. 556–562.

Gartry et al., "Excimer Laser Photorefractive Keratectomy", Ophthalomology, Aug. 1992, pp. 1210–1219.

Gilbert, "Corneal Topography: In Search of the Excimer Islands", Eye Care Technology, Oct. 1993, pp. 23–28.

L'Esperance, "New Laser Systems, Their Potential Clinical Usefulness, and Investigative Laser Procedures", Opthalmic Lasers, 1989, pp. 995–1045.

Lin et al, "Corneal Topography Following Excimer Photorefractive Kerectomy for Myopia", Journal of Cataract Refractive Surgery, 1993, pp. 149–154.

Lin et al, "A Multiwavelength Solid State Laser for Ophthalmic Applications", Ophthalmic Technologies, Jun. 1992, pp. 266–275.

Marguerite B. McDonald et al, "Central Refractuive Keratectomy for Myopia", Ophthalmology, Sep. 1991, pp. 1327–1337.

Marshall et al, "Long–term Healing of the Central Cornea after Photorefractive Keratectomy Using an Excimer Laser", Oct. 1998, pp. 1411–1421.

Marshall et al, "Photoablative Reprofilling of the Cornea Using an Excimer Laser: Photorefractive Keratectomy", Lasers in Ophthalmology, Jan. 1986, pp. 21–48.

McDonald et al., "Central Photorefractive Keratectomy for Myopia", Arch Ophthalmology, Jun. 1990, pp. 799–808.

Palikaris et al, "Excimer Laser In Situ Keratomileusis and Photorefractive Karatectomy for Correction of High Myopia"Journal of Refractive and Corneal Surgery, Sep. 1994, pp. 498–510.

Ren et al, "Corneal Refractive Surgery Using an Ultra–Violet (213nm) Solid State Laser" Ophthalmic Technologies, Jun. 1991, pp. 129–139.

Rozakis, "Refractive Lamellar Keratoplasty" History of Keratomileusis, 1994, Chapt. 1–13.

Seiler et al, "Excimer Laser (193nm) Myopic Keratomileusis in Sighted and Blinded Human Eyes" Refractive and Corneal Laser Surgery, Jun. 1990, pp. 165–173.

Serdarevic, "Corneal Laser Surgery", Ophthalmic Lasers, 1989, pp. 919–970.

Steinert et al, "Laser Corneal Surgery", Laser Research Laboratory, 1998, pp. 151–154.

Thompson et al, "Philosophy and Technique for Excimer Laser Phototherapeutic Keratectomy", Refractive and Corneal Surgery, Apr. 1993, pp. 81–85.

Trokel et al Excimer Laser Surgery of the Cornea, American Jounral of Ophthalmology, Dec. 1983, pp. 710–715.

Trockel et al, "Evolution of Excimer Laser Corneal Surgery", Jul. 1989, pp. 373–381.

Van Mielaert et al, "On the Safety of 193–Nanometer Excimer Laser Refractive Corneal Surgery" Refractive and Corneal Surgery, Jun. 1992, pp. 235–239.

Wilson et al, "Changes in Corneal Topography after Excimer Laser Photorefractive Keratectomy for Myopia", Ophthalmology, Spe. 1991, pp. 1338–1347.

SMOOTH AND UNIFORM LASER ABLATION APPARATUS AND METHOD

BACKGROUND OF THE INVENTION

1. Field of the Invention

This invention relates generally to a method and apparatus for scanning an ablating laser beam to ablate tissue. More particularly, it relates to a method and apparatus for scanning an ablating laser beam to ablate corneal tissue resulting in improved smoothness and uniformity of the remaining tissue.

2. Description of Related Art

The ablation of human tissue with an ablating laser beam is known. Typically, a laser beam is scanned across rows of ablation points in an ablation zone of a layer of tissue to be ablated, and adjacent points or spots in each row are sequentially ablated to reshape the underlying tissue.

For example, laser ablation is utilized to reshape a cornea of an eye to correct refractive disorders. In a normal human eye, the cornea bends or refracts incoming light rays causing light rays to focus on the retina of the eye. Improper refraction of incoming light rays causes blurred vision or a refractive disorder. Myopia (nearsightedness) is one of the most common refractive disorders. In a nearsighted eye, the cornea is too steep, causing light rays to be focused in front of the retina, not at the retina, causing distant objects to appear blurred.

To correct nearsightedness, laser vision correction, e.g., Photorefractive Keratectomy (PRK), can be performed to make the cornea less steep. In PRK, an ablating laser beam removes successive layers of corneal tissue from an ablation zone of a cornea. Each layer of corneal tissue is removed by ablating the corneal tissue with a series of adjacent laser beam pulses disposed generally along a linear path (e.g., a row). By reshaping the cornea to be less steep, light rays focus properly on the retina of the eye, and the nearsightedness condition is corrected.

Conventional laser ablation for vision correction has achieved good results, with the majority of patients no longer being dependent on corrective lenses after the treatment. However, rough or non-uniform tissue remaining after the treatment may cause imperfect results detracting from the full potential of the laser ablation treatment. Thus, the present inventors have recognized that it is important to achieve a smooth and uniform ablation such that remaining tissue does not contain any significant ridges or other rough areas therein.

It is known that the patient's eye moves when undergoing ophthalmic refractive laser surgery. Thus, full treatments are typically performed in a short amount of time, e.g., in under one minute, to minimize the effect of the movement of the eye. Nevertheless, predetermined sequential scans of the ablating laser beam may over ablate some areas and under ablate other areas due to the movement of the eye during the ablation procedure. Therefore, the remaining tissue may not be as smooth or uniform as planned.

FIG. 1 shows a conventional scan pattern across an ablation zone.

In FIG. 1, an ablation layer, defined by ablation zone 135, of a patient's eye that ideally remains stationary during an ablation treatment of an ablating laser beam, is scanned with an ablating laser beam across rows 1 to 10, from left to right. If the eye remains stationary, the ablation points are distributed evenly throughout the ablation zone, and the remaining corneal tissue will be relatively smooth and uniform.

FIG. 2 shows the same ablation zone 135 as in FIG. 1, but as resulting when the patient's eye has moved downwardly at the end of the third scanning line 3. As a result, the fourth and fifth scanning lines 4, 5 as shown in FIG. 2 are scanned on previously ablated areas of the ablation zone 135 instead of at the proper, or planned location as shown in FIG. 1.

Then, before the sixth scanning line 6, the patient's eye moves back to the correct or intended position, and proper or intended ablation continues.

As a result of the eye movements noted above, the corneal surface is ablated too deeply in certain portions thereof (i.e., between the first and third scan lines 1, 3) and is ablated too shallowly in another portion of the cornea (i.e., between the third and sixth scan lines 3, 6). This results in a rough and/or non-uniform surface on the remaining corneal tissue.

The ablation points shown in FIG. 1 and FIG. 2 represent the center of each ablating laser beam pulse. Significant ablation overlap can occur when the ablating laser beam is larger than the distance between each ablation point. However, when the eye moves during corrective eye surgery, the resulting or actual location of the scanned ablation points with respect to the ablation zone 135 is significantly deeper than other properly scanned ablation points, while other portions of the corneal tissue may not have been ablated as intended. This may result in uneven, rough and/or non-smooth ridges on the cornea.

Even if the patient's eye does not move during the ablation procedure, an uneven distribution of ablating laser beam pulses can cause roughness on the cornea.

Accordingly, there exists a need for a method and apparatus for scanning an ablating laser beam which smoothly and uniformly ablates tissue in the face of real-world conditions, e.g., a moving eye.

SUMMARY OF THE INVENTION

An object of the invention is to provide a method of ablating tissue fulfill the need referred to above. In accordance with the principles of the present invention, this objective is obtained by providing a method of ablating tissue including defining a plurality of scan lines in an ablation zone on the tissue and defining a plurality of laser beam ablation points along each of the scan lines. An ablating laser beam is scanned along a series of non-adjacent scan lines of the plurality of scan lines and tissue is ablated at non-adjacent ones of the laser beam ablation points on each non-adjacent scan line of the series of non-adjacent scan lines. An apparatus for performing the method is also provided.

In another aspect of the invention, the above objective is obtained by dividing an ablation zone into a plurality of domains. An average depth of ablation in each of the domains is determined. Tissue is ablated by controlling a number of ablating laser beam pulses in each domain in proportion to the average depth of ablation in each domain. An apparatus is disclosed for performing this method.

BRIEF DESCRIPTION OF THE DRAWINGS

Features and advantages of the present invention will become apparent to those skilled in the art from the following description with reference to the drawings, in which.

DETAILED DESCRIPTION OF ILLUSTRATIVE EMBODIMENTS

The present invention provides a method and apparatus for performing laser ablation to remove or reshape human tissue, e.g., corneal tissue in a cornea of an eye. Although the embodiments of the present invention are described with reference to the removal of corneal tissue, the present invention relates to laser ablation techniques of human tissue in general. Moreover, with respect to the application of the present invention for the reshaping of a cornea, the method and apparatus of the present invention further relates to use in laser refractive keratectomy (e.g., photorefractive keratectomy or PRK, PRK after radial keratotomy, laser keratectomy with mircrokeratome, intrastromal photodisruption), laser therapeutic keratectomy, and/or laser lamellar resection.

The method and apparatus of the present invention, when applied to vision correction, provides several techniques to achieve smoother and more uniform ablation than is currently known, especially if the patient's eye moves during the vision correction surgery.

Basically, with laser ablation techniques, when more laser energy is deposited on the desired position on the tissue to be ablated, more tissue is removed and when less energy is deposited on the desired position on the tissue, less tissue is removed. A layer of the tissue is removed by ablating specific ablation points or spots in a predetermined ablation zone of the tissue.

The method and apparatus of the present invention scans a laser beam across an ablation zone 135 on a cornea of an eye in a predetermined scan pattern selected in accordance with the desired ablation rate. However, rather than ablating tissue at each successive, adjacent ablation point along each scan line of a predetermined pattern, the present invention provides for intermittent multiple passes along non-adjacent scan lines through the ablation zone 135. The term "intermittent" herein refers to non-adjacent ablation points or spots along a single linear scan or pass through the ablation zone 135. Thus, importantly, the present invention provides for non-sequential ablation of ablation points along a predetermined scanning pattern.

Thus, in accordance with the principles of the present invention, subsequent pass(es) along the same scan lines are performed to cause ablation at non-adjacent ablation points, e.g., between those points already ablated in a previous pass through the scan line through the ablation zone 135.

The intermittent nature of the ablation, i.e., ablating every other, every third, every fourth, etc., ablation point in any one pass through a scan line of the ablation zone, and/or ablating every other, every third, every fourth, etc., scan line, results in a smooth and uniform tissue surface remaining after the ablation procedure, even in the face of eye movement, as compared to conventional methods and scan patterns.

Figure 1:
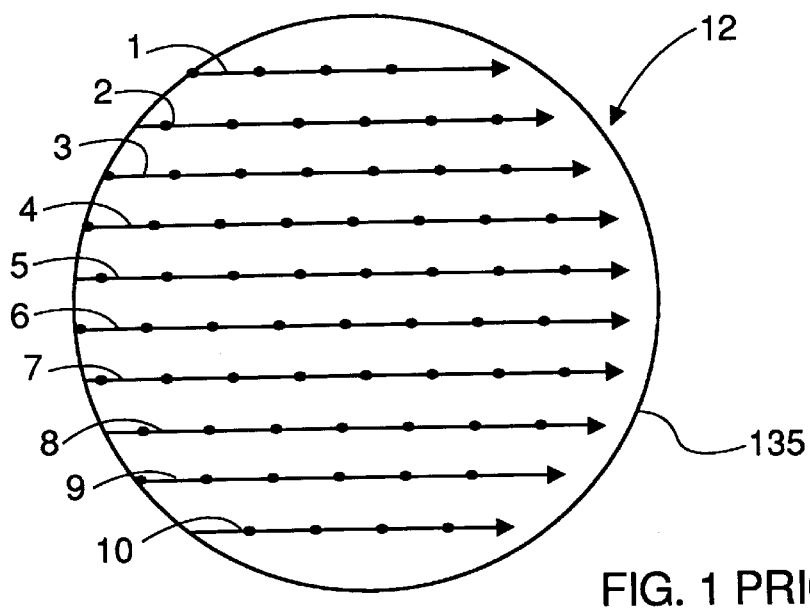
FIG. 1 is a top plan view illustrating a conventional scanning pattern of an ablating laser beam over an ablation zone wherein the patient's eye remains stationary throughout the performance of the ablation through the scanning pattern.
Figure 2:
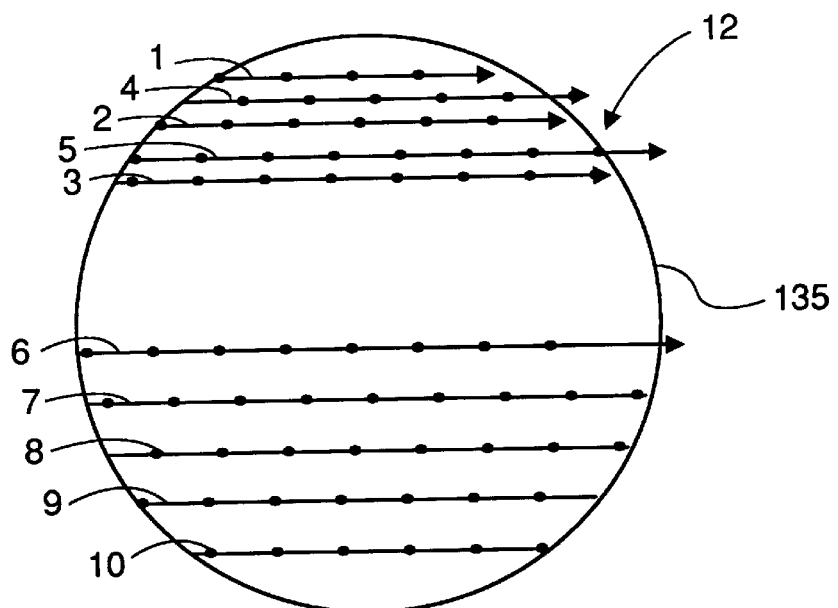
FIG. 2 is a top plan view illustrating a conventional resulting pattern of an ablating laser beam over an ablation zone wherein the patient's eye moves during the performance of the ablation through the intended scanning pattern shown in FIG. 1.
Figure 3:
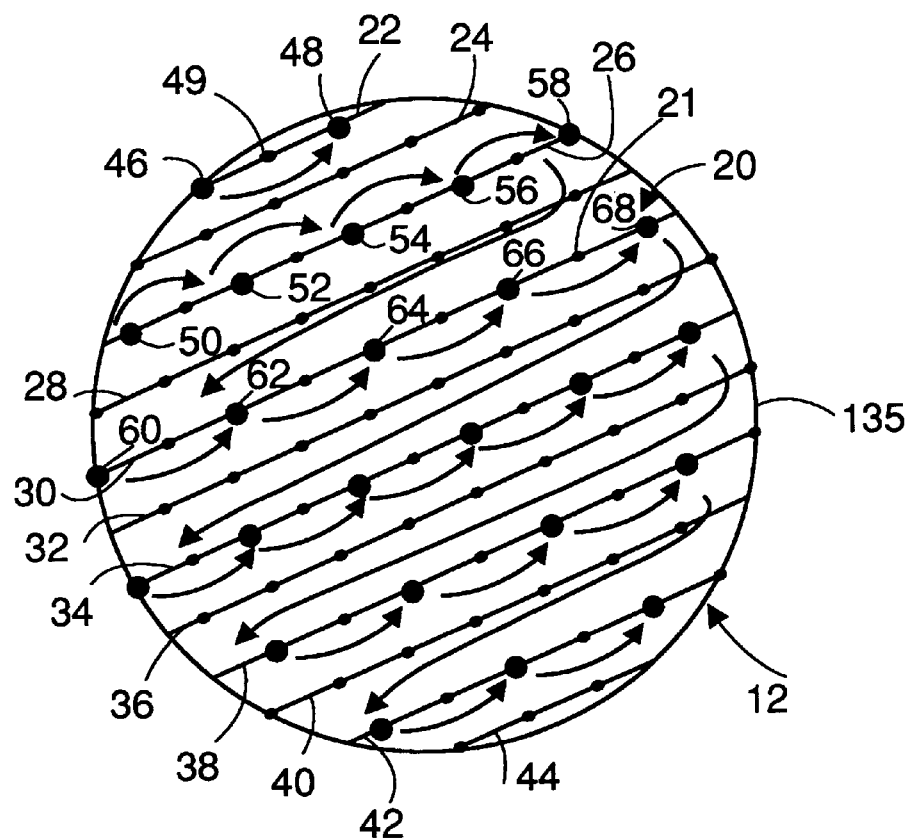
FIG. 3 is a top plan view illustrating the location of ablation points on scan lines in an ablation zone using a scanning technique in accordance with the principles of the present invention.

FIG. 3 shows intermittent ablation of a predetermined scanning pattern in accordance with the principles of the present invention.

As illustrated in FIG. 3, the present invention includes linear scanning patterns on an ablation zone of a cornea. However, the temporal order of the ablation points is changed to achieve a smoother and more uniform reshaping of the cornea surface, even when the patient's eye moves during the ablation procedure.

In particular, FIG. 3 illustrates a scanning pattern consisting of twelve (12) scan lines 22, 24, 26, 28, 30, 32, 34, 36, 38, 40, 42, and 44.

In a linear overlapping intermittent ablation pattern performed in accordance with one embodiment of the present invention only one-fourth (¼) of the ablation points in a single layer are ablated during a first pass through the scan lines of the ablation zone 135. An arbitrary starting point is selected and a first series of scan lines in the ablation zone 135 are selected for ablation. For example, a first series of non-adjacent scan lines may be selected to include scan lines 22, 26, 30, 34, 38 and 42. As used herein, "non-adjacent scan lines" means scan lines that are not directly adjacent, e.g., scan lines 22 and 26 are non-adjacent since at least one scan line 24 is disposed between scan lines 22 and 26.

To begin the ablation procedure, non-adjacent laser beam ablation points 46, 48, in scan line 22 are ablated. As used herein, "non-adjacent laser beam ablation points" means laser beam ablation points that are not directly adjacent, e.g., at least one point, e.g., point 49, is disposed between points 46 and 48.

Next, by scanning non-adjacent laser beam ablation points on every other scan line of the plurality of scan lines, e.g., on every scan line of the first series of scan lines, non-adjacent laser beam ablation points 50, 52, 54, 56, 58 on scan line 26 are scanned and ablated, non-adjacent laser beam ablation points 60, 62, 64, 66, 68 on scan line 30 are scanned and ablated, etc. until one-fourth of the overall ablation layer in the ablation zone 135 is scanned.

After the entire first one-quarter (¼) of the first layer is scanned and certain non-adjacent ablation points are ablated on the first series of scan lines, the next one-quarter (¼) of the first layer is scanned and non-adjacent ablation points not previously ablated on each scan line of the first series of scan lines are ablated. Thereafter, a second series of scan lines are selected which include scan lines 24, 28, 32, 36, 40, and 44. Every other ablation point on each scan line of the second series of scan lines is then ablated. This process is repeated to ablate ablation points not previously ablated on each scan line of the second series to complete the overall ablation of the first layer of the ablation zone 135. Moreover, subsequent layers of corneal tissue within the ablation zone 135 may be ablated using the above-described procedure of the invention.

It can be appreciated that if the patient's eye does not move during the ablation process, the end result of the ablation in accordance with the principles of the present invention will result in approximately the same evenness and uniformity as resulting from a conventional ablation method and apparatus. However, if the patient's eye moves during the ablation procedure, which generally occurs, the result of the method of the present invention is a smoother and more uniform reshaping of the cornea.

The linear overlapping intermittent ablation method of the present invention can be employed by skipping additional laser beam ablation points, such as scanning and ablating only every third point, skipping two (2) scan lines instead of only skipping one (1) scan line, etc.

A second aspect of the present invention which provides a smooth and uniform ablation is referred to herein as a random overlapping intermittent ablation. As illustrated in FIG. 3, this embodiment comprises following a certain regular scan line pattern as described above, but with a random order of non-adjacent laser beam ablation points and non-adjacent scan lines.

Figure 5:
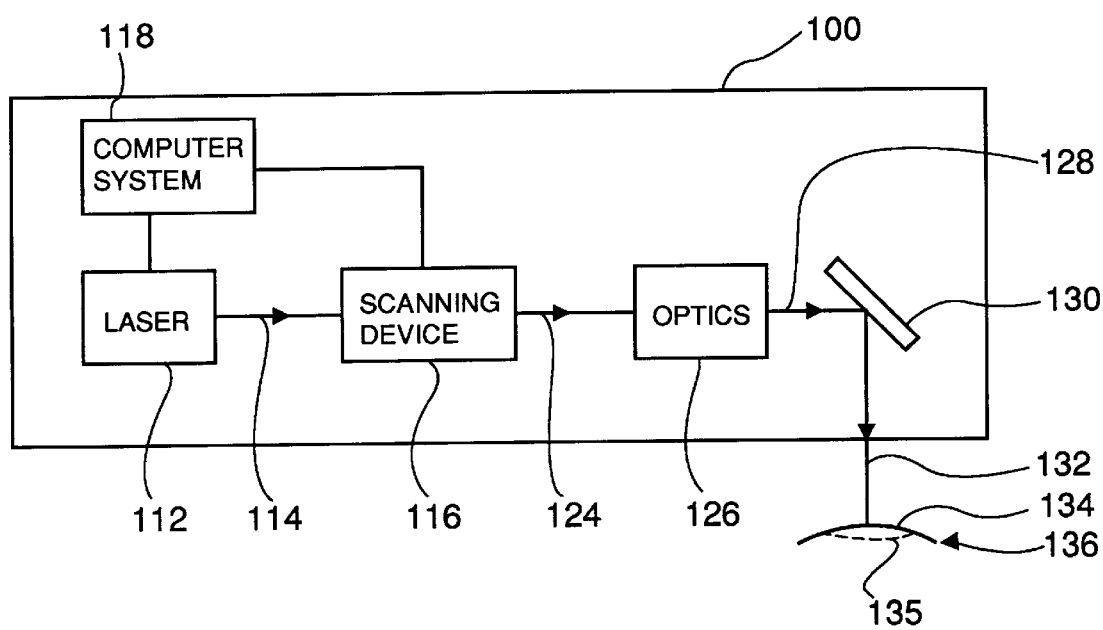
FIG. 5 is a schematic illustration of a laser device for ablating tissue provided in accordance with the principles of the present invention.

FIG. 5 shows a laser device for ablating tissue provided in accordance with the principles of the present invention.

In FIG. 5, a laser ablation device 100 includes a laser 112 operable to produce a pulsed ablating laser beam 114, which is directed to a scanning device 116. The scanning device 116 is operatively connected to a computer system 118 for control thereby. The computer system 118 can be located within the laser device 100, or external thereto. The laser 112 can also be operatively connected to the computer system 118 for control thereby.

The scanning device 116 of the laser device 100 of the present invention is operable to control the scanning of the pulsed ablating laser beam 114 across an ablation zone 135 on the cornea 134 of a patient's eye 136. In particular, a scanned laser beam 124 departs the scanning device 116 and is directed to other optics components 126 which may be utilized for shaping the scanned beam 124 in a desired manner. A shaped scanned beam 128 may then be directed to a reflecting mirror 130. A reflected beam 132 is directed from the reflecting mirror 130 onto an ablation zone 135 of a cornea 134 of a patient's eye 136.

The various portions of the laser device 100 can be constructed, e.g., in accordance with the laser device described in U.S. Pat. No. 5,520,679, the disclosure of which is hereby explicitly incorporated herein by reference. Of course, the computer system 118 of the present invention controls the scanning device 116 through a scanning pattern in accordance with the principles of the present invention.

The laser device 100 is constructed and arranged to scan an ablation zone 135 and ablate tissue at certain ablation points within the ablation zone 135. The tissue to be ablated is divided into a number of successive layers in the ablation zone 135, each layer typically being ablated individually, one after the next. In operation, the laser beam 132 is directed toward the tissue to be ablated, and the laser device 100 is intermittently activated or allowed to pass to produce a predetermined amount of laser beam energy at intermittent ablation points 20, e.g., in a linear scan pattern.

In operation, all of the laser beam ablation points of the scanning pattern for an entire layer or all of the laser beam ablation points of the scanning pattern for all of the layers can be predetermined in the computer system 118. Next, the computer system 118 of the laser device 100 is controlled to selectively or randomly order the intermittent ablation of laser beam ablation points.

A third aspect of the present invention which provides a smooth and uniform ablation is referred to herein as a probability overlapping intermittent ablation. It should be understood that the probability overlapping intermittent ablation technique does not follow a layer concept or a linear or circular scanning method. The probability overlapping intermittent ablation technique directs a certain number of laser pulses to a certain laser beam ablation point on the cornea or other tissue proportional to the depth of ablation required at that laser beam ablation point.

Figure 4:
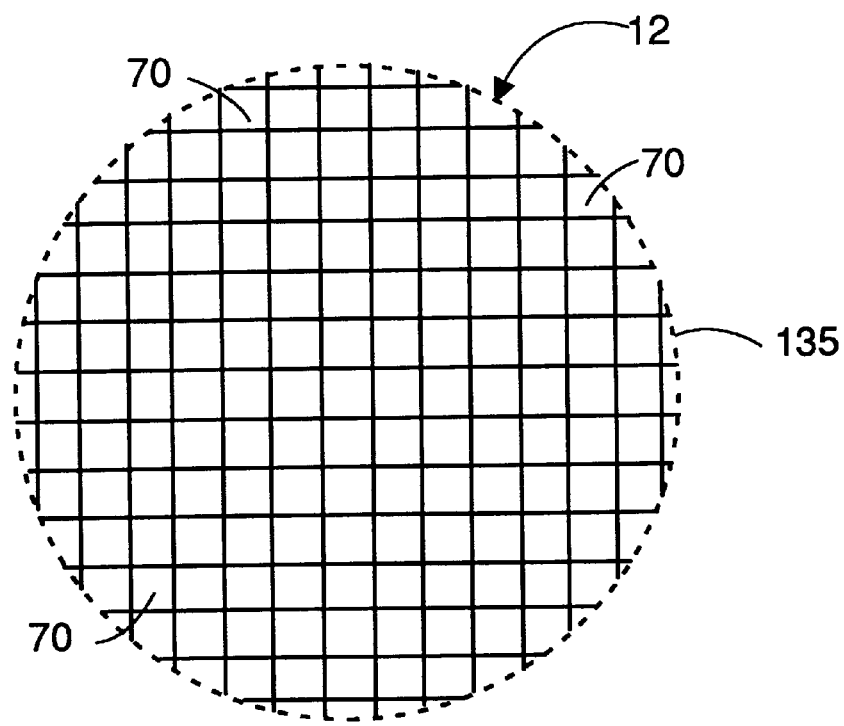
FIG. 4 is a top plan view illustrating the resulting pattern of an ablation zone divided into a predetermined number of domains, and scanned in accordance with the principles of the present invention.

As illustrated in FIG. 4, with this third aspect, the ablation zone 135 of the cornea is divided into small domains 70 such as squares, triangles, hexagons, or other shapes. The depth of ablation at the center of each domain 70 is considered the average depth for that particular domain 70.

In operation, it is necessary to calculate the total number of laser beam pulses necessary for the entire ablation procedure. First, the total volume V of tissue to be removed for the entire surgery is calculated by the surgeon according to the initial conditions such as the diopter of correction, ablation zone size, the initial radius of curvature of the eye, etc. Next, the tissue volume v each laser beam pulse removes is calculated from either the laser pulse characteristics (energy, beam size, pulse duration, etc.), or from experimental data (ablation on plastic or other calibration material). The total number of laser beam pulses required for the surgery can be determined from the equation $N=V/v$. It should be noted that N can be in the order of many thousands, depending on the laser pulse energy and the amount of ablation required. The number of laser beam pulses in the "ith" domain is given by $n_i=kNd_i$, where $d_i$ is the average depth in the "ith" domain, and k is the proportionality factor given by $N=n_i=kNd_i$, or $k=1/(d_i)$.

The number of laser beam pulses delivered to each domain 70 is proportional to the average depth of ablation in that domain 70. It is important when utilizing this third aspect that the area of treatment be divided into many domains, with the size of each domain 70 being sufficiently small such that the ablation depth profile will closely and smoothly fit the theoretical profile.

A computer can distribute the laser beam pulses to optimize the result. For example, the computer system 118 of the laser device 100 can be programmed to require that no greater than two (2) pulses will hit the same ablation point in any one domain, that the distribution of pulses in each domain is even and uniform, and that the distributions near and at the border lines of the domains are relatively uniform, without more than two (2) pulses hitting any same ablation point. By following this technique, the overall even distribution of laser pulses will result in a smooth and uniformly ablated corneal surface even if the patient's eye moves during surgery. Furthermore, since scanning and finishing one domain 70 after another would result in an extremely rough cornea surface if the eye moves, the temporal order of the ablation of the ablation points in the predetermined scanning pattern randomized by the computer system 118 should be calculated before the actual ablation treatment of the cornea begins.

It will be understood by those of ordinary skill in the art that, depending on the desired and required amount of ablation, the number of scan lines within the ablation zone can be increased or decreased. Furthermore, the ablation pattern can overlap successive layers to be ablated within the ablation zone 135.

In all embodiments, the laser beam ablation points represent the center point of an ablating laser beam on the surface of the tissue to be ablated. However, those of ordinary skill in the art will appreciate that the energy of the laser beam typically extends beyond the bounds of the depicted laser beam ablation points or spots causing areas of ablated tissue to overlap. The overlapping of the ablated tissue and/or the number of laser beam ablation points or spots in the ablation zone can be empirically determined to yield optimum results, i.e., surface smoothness, uniformity, accuracy of reshaping, etc.

The foregoing exemplary descriptions and the illustrative embodiments of the present invention have been shown in the drawings and described in detail, with varying modifications and alternative embodiments being taught. While the invention has been so shown, described and illustrated, it should be understood by those skilled in the art that changes in form and detail may be made therein without departing from the true spirit and scope of the invention, and that the scope of the present invention is to be limited only by the appended claims.

What is claimed is:

1. A method of ablating tissue with an ablating laser beam, the method comprising:
   defining a plurality of scan lines in an ablation zone on said tissue;
   defining a plurality of laser beam ablation points along each of said scan lines; and
   scanning said ablating laser beam along a series of non-adjacent ones of said plurality of scan lines and ablating said tissue at non-adjacent ones of said laser beam ablation points.

2. The method of ablating tissue according to claim 1, further including:
   scanning said ablating laser beam along said series of non-adjacent ones of said plurality of scan lines and ablating said tissue at non-adjacent ones of said laser beam ablation points not previously ablated.

3. The method of ablating tissue according to claim 2, further including:
   scanning said ablating laser beam along a second series of non-adjacent ones of said plurality of scan lines and ablating said tissue at non-adjacent ones of said laser beam ablation points.

4. The method of ablating tissue according to claim 3, further including:
   scanning said ablating laser beam along said second series of non-adjacent ones of said plurality of scan lines and ablating said tissue at non-adjacent ones of said laser beam ablation points not previously ablated.

5. The method of ablating tissue according to claim 1, wherein:
   ablation is performed during each pass of said non-adjacent ones of said plurality of scan lines at a spacing of at least every other laser beam ablation point.

6. The method of ablating tissue according to claim 1, wherein:
   said series of non-adjacent ones of said plurality of scan lines comprises every other scan line of said plurality of scan lines defined in said ablation zone.

7. The method of ablating tissue according to claim 1, further comprising:
   randomizing an order of scanning of said non-adjacent ones of said laser beam ablation points.

8. The method of ablating tissue according to claim 1, further comprising:
   randomizing an ablation order of said non-adjacent ones of said plurality of scan lines of said series.

9. The method of ablating tissue according to claim 1, wherein said ablated tissue is corneal tissue.

10. A method of ablating tissue with an ablating laser beam, the method comprising:
    dividing an ablation zone into a plurality of domains;
    determining an average depth of ablation in each of said domains; and
    ablating said tissue by controlling a plurality of ablating laser beam pulses in each of said plurality of domains in proportion to said average depth of ablation in each of said plurality of domains.

11. A method of ablating tissue with an ablating laser beam, the method comprising:
    defining a plurality of scan lines in an ablation zone on said tissue;
    defining a plurality of laser beam ablation points along each of said plurality of scan lines; and
    scanning said ablating laser beam along a series of non-adjacent ones of said plurality of scan lines.

12. The method of ablating tissue with an ablating laser beam according to claim 11, further comprising:
    scanning said ablating laser beam along said plurality of scan lines at non-adjacent ones of said laser beam ablation points.

13. A method of ablating tissue with an ablating laser beam, the method comprising:
    defining a plurality of scan lines in an ablation zone on said tissue;
    defining a plurality of laser beam ablation points along each of said plurality of scan lines; and
    scanning said ablating laser beam along said plurality of scan lines at non-adjacent ones of said laser beam ablation points.

14. The method of ablating tissue with an ablating laser beam according to claim 13, further comprising:
    scanning said ablating laser beam along a series of non-adjacent ones of said plurality of scan lines.

15. Apparatus for ablating tissue with an ablating laser beam, comprising:
    means for defining a plurality of scan lines in an ablation zone on said tissue;
    means for defining a plurality of laser beam ablation points along each of said plurality of scan lines; and
    means for scanning said ablating laser beam along a series of non-adjacent ones of said plurality of scan lines.

16. The apparatus for ablating tissue with an ablating laser beam according to claim 15, further comprising:
    means for scanning said ablating laser beam along said plurality of scan lines at non-adjacent ones of said laser beam ablation points.

17. Apparatus for ablating tissue with an ablating laser beam, comprising:
    means for defining a plurality of scan lines in an ablation zone on said tissue;
    means for defining a plurality of laser beam ablation points along each of said plurality of scan lines; and
    means for scanning said ablating laser beam along said plurality of scan lines at non-adjacent ones of said laser beam ablation points.

18. The apparatus for ablating tissue with an ablating laser beam according to claim 17, further comprising:
    means for scanning said ablating laser beam along a series of non-adjacent ones of said plurality of scan lines.

19. A method of ablating tissue with an ablating laser beam, the method comprising:
    defining an ablation pattern forming a plurality of pattern lines in an ablation zone on said tissue;
    defining a plurality of overlapping laser beam ablation points along each of said pattern lines; and
    randomly scanning said ablating laser beam in said ablation pattern to ablate a first series of non-adjacent ones of said laser beam ablation points.

20. The method of ablating tissue with an ablating laser beam according to claim 19, further comprising:
    randomly scanning said ablating laser beam in said ablation pattern to ablate a second series of non-adjacent ones of said laser beam ablation points.

21. The method of ablating tissue with an ablating laser beam according to claim 20, wherein:

individual ones of said first series of non-adjacent ones of said laser beam ablation points being adjacent to individual ones of said second series of non-adjacent ones of said laser beam ablation points.

* * * * *